United States Patent
Noblett et al.

(10) Patent No.: US 12,396,756 B2
(45) Date of Patent: Aug. 26, 2025

(54) CONVERSION KIT FOR AN EXTERNAL FIXATION SYSTEM

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Andrew P. Noblett, Bartlett, TN (US); Johnny R. Mason, Bartlett, TN (US); Paul Bell, Memphis, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, CH Singapore (SG)

( * ) Notice: Subject to any disclaimer, the term of this patent is extended or adjusted under 35 U.S.C. 154(b) by 520 days.

(21) Appl. No.: 17/911,001

(22) PCT Filed: Apr. 12, 2021

(86) PCT No.: PCT/US2021/026862
§ 371 (c)(1),
(2) Date: Sep. 12, 2022

(87) PCT Pub. No.: WO2021/211443
PCT Pub. Date: Oct. 21, 2021

(65) Prior Publication Data
US 2023/0090626 A1    Mar. 23, 2023

Related U.S. Application Data

(60) Provisional application No. 63/010,294, filed on Apr. 15, 2020.

(51) Int. Cl.
*A61B 17/62* (2006.01)
*A61B 17/64* (2006.01)

(52) U.S. Cl.
CPC ............ *A61B 17/62* (2013.01); *A61B 17/645* (2013.01); *A61B 17/6475* (2013.01)

(58) Field of Classification Search
CPC ......... A61B 17/60; A61B 17/62; A61B 17/64; A61B 17/6425; A61B 17/6433; A61B 17/645; A61B 17/66
See application file for complete search history.

(56) References Cited

U.S. PATENT DOCUMENTS 5,681,309 A * 10/1997 Ross, Jr. ................ A61B 17/62
                                                                606/56
9,101,398 B2 * 8/2015 Singh .................... A61B 17/62
(Continued)

FOREIGN PATENT DOCUMENTS

CN    110495937 A * 11/2019 ............. A61B 17/62
WO      9730650 A1    8/1997

OTHER PUBLICATIONS

Smith & Nephew, Inc., Jet-X External Fixator brochure "Ankle Spanning, Knee Spanning, Long Bone and Pelvice", dated Sep. 2012.
(Continued)

*Primary Examiner* — Eduardo C Robert
*Assistant Examiner* — Michelle C Green
(74) *Attorney, Agent, or Firm* — KDW Firm PLLC

(57) ABSTRACT

A kit and corresponding methods of use are disclosed. In use, the kit includes a plurality of articulating clamps for coupling to one of the rings of an external fixation system. In use, the clamps include a body portion having a stem arranged and configured to be received within an opening formed in one of the rings. The clamp further including a clamp assembly for engaging a rod spanning the first and second rings. Thus arranged, the clamp may be directly coupled to one of the rings and the rod, the clamp enabling the position of the ring to be adjusted relative to the rod. As
(Continued)

such, the clamps may enable, inter alia, a hexapod external fixation system to be converted into a static frame, a static frame to be constructed in a more efficient manner, and/or creation of an enlarged visualization or working window.

28 Claims, 11 Drawing Sheets

(56) References Cited

U.S. PATENT DOCUMENTS

| | | | |
|---|---|---|---|
| 10,390,859 B2* | 8/2019 | Sakkers | A61B 17/62 |
| 2007/0055234 A1* | 3/2007 | McGrath | A61B 17/62 |
| | | | 606/56 |
| 2018/0368887 A1 | 12/2018 | Lauf et al. | |

OTHER PUBLICATIONS

International Search Report and Written Opinion dated Jul. 22, 2021, for PCT/US2021/026862 (13 pages).

* cited by examiner

CONVERSION KIT FOR AN EXTERNAL FIXATION SYSTEM

CROSS-REFERENCE TO RELATED APPLICATIONS

This application is a National Phase filing of International Application No. PCT/US2021/026862, filed Apr. 12, 2021, which application is a non-provisional of, and claims the benefit of the filing date of, U.S. provisional patent application No. 63/010,294, filed Apr. 15, 2020, entitled "Conversion Kit for an External Fixation System," the entirety of which application is incorporated by reference herein.

FIELD OF THE DISCLOSURE

The present disclosure relates generally to orthopedic devices, systems, and methods for facilitating fracture alignment, and particularly to a kit and methods for converting a hexapod external fixation system into a static, or at least partially static, external fixation system, for enabling temporary removal of one or more struts from a hexapod external fixation system to provide a larger visualization and/or working window, and/or for enabling construction of a static frame with increased flexibility (e.g., a static frame with increased options when constructing the static frame).

BACKGROUND OF THE DISCLOSURE

People suffer bone fractures each year. In many instances, a person that suffers a bone fracture is required to use a bone alignment device such as, for example, an external fixation system, to align two or more bones, bone fragments, bone pieces, bone segments, bone portions, etc. (used interchangeably herein without the intent to limit).

One common type of external fixation system is known as a hexapod external fixation system. Generally speaking, hexapod external fixation systems allow for polyaxial movement of the coupled bone segments and are typically used to keep fractured bone segments stabilized and in alignment during a treatment period. Referring to FIG. 1, an example embodiment of a hexapod external fixation system 100 is shown. As shown in FIG. 1, the hexapod external fixation system 100 forms a generally circular, metal frame with a first ring, frame, base, etc. (used interchangeably herein without the intent to limit) 102 and a second ring 104 connected by six adjustable length struts 106 (labeled as struts 106-1 through 106-6 in FIG. 1). Each strut 106 may be independently lengthened or shortened relative to the rest of the frame, thereby allowing for six different axes of movement. As shown, the hexapod external fixation system 100 includes six adjustable length struts 106 positioned around about the first and second rings 102, 104 at various angles relative to one another.

In use, the hexapod external fixation system 100 may be used to treat a variety of skeletal fractures of a patient. Typically, the hexapod external fixation system 100 is positioned around the patient's bone segments and is used to align two or more bone segments. To do so, a length of each strut 106 may be incrementally adjusted (e.g., shortened or lengthened) in accordance with a prescription or treatment plan (used interchangeably herein without the intent to limit) that specifies adjustments to be made to each strut 106 over time to ensure successful bone alignment. In many instances, the length of each strut 106 should be adjusted daily to comply with the provided prescription. Adjusting the length of each strut 106 adjusts the distance between the first and second rings 102, 104. That is, as the lengths of the struts 106 are adjusted, the first and second rings 102, 104 may be brought closer together or moved farther apart. One known example of a hexapod external fixation system is the Taylor Spatial Frame manufactured and sold by Smith Nephew, Inc.

In use, treatment with a hexapod external fixation system involves two phases. The first phase can be referred to as an adjustment phase. During the adjustment phase, the patient is adjusting the plurality of struts on, for example, a daily basis per the prescription to achieve the desired bone alignment. The second phase can be referred to as a consolidation phase. During the consolidation phase, the bone segments have been properly positioned and adjustments are no longer needed. In the consolidation phase, the hexapod external fixation system remains coupled to the patient's bone segments while the bone segments consolidate (e.g., heal and harden).

One known disadvantage associated with hexapod external fixation systems 100 is given the arrangement of the struts 106 along with the size (e.g., diameter) of the struts 106, X-ray visualization of the patient's anatomy (e.g., bone segments) may be obscured. As such, imaging of the patient's anatomy to determine if a patient's bone segments are properly healing is rendered more difficult (e.g., one or more struts may obscure proper visualization of the patient's underlying anatomy).

As a result, some health care providers may elect to remove one or more struts from a hexapod external fixation system to provide increased visibility. However, this suffers from the drawback that the frame is now destabilized and may result in patient discomfort and pain. Alternatively, some health care providers may elect to remove the hexapod external fixation system entirely and replace it with a static frame (e.g., in use, the first and second rings 102, 104 may remain, but the adjustable length struts 106 may be exchanged (e.g., removed and replaced) with static members or struts (e.g., threaded rods with nuts). Alternatively, given the nature of a patient's injuries, a static frame may be implanted at the outset. Generally speaking, a static frame includes first and second rings connected by, for example, parallel struts or rods. For example, in one well known system, first and second rings are coupled to each other by four threaded rods (e.g., threaded rods and nuts are used to couple the first and second rings together). In use, the first and second rings in a static frame are positioned close to parallel relative to each other in order to receive the threaded rods (e.g., generally speaking, a static frame may accommodate some angulation of the first and second rings relative to each other by utilizing, for example, conical washers, but even in these instances, the amount of angulation is generally limited to approximately ±14 degrees). As a result, constructing a static frame (e.g., positioning and implanting a static frame) is difficult and time-consuming.

In addition, and/or alternatively, for one or more reasons, a health care provider may desire to "dynamize" an external fixation system (e.g., enabling micro-motion of the frame, etc.) during the consolidation phase. By providing dynamization of the external fixation system, improved bone stimulation and healing can be achieved. In the past, to provide dynamization of a static frame, two nuts may be used in connection with each threaded rod (e.g., a first nut is positioned on one side of the ring while a second nut is positioned on the other side of the ring). By providing a gap between the ring and the nuts, the ring can move (e.g., translate) by a small amount along a length of the threaded rod. To provide dynamization of a hexapod external fixation system, one or more of the struts may be unlocked thereby enabling the strut to telescope. Alternatively, a health care provider may even elect to remove one of the struts thereby destabilizing the frame. However, given the angled nature of the struts in a hexapod external fixation system, neither of these methods produce pure, or substantially pure, axial dynamization. Rather, these methods produce non-axial dynamization such that some amount of shear and/or torsion is introduced into the system at the healing site (e.g., these methods do not produce pure axial compression and decompression, which is the goal of dynamization). As a result, risk of fracture of the healing bone is increased.

Moreover, in use, during, for example, the adjustment phase of a hexapod external fixation system, the prescription may require the spacing of the first and second rings to have a large workable range including a very small minimum distance apart and/or a very large maximum distance apart. Many struts are unable to meet the entire workable range specified by the prescription. As a result, the struts are often changed out one or more times with new struts to accommodate the full workable range of the external fixation system specified by the prescription. Changing out the struts of the external fixation system may be tedious and may be uncomfortable to the patient. That is, removing one or more struts for either a larger or smaller length strut destabilizes the external fixation system such that the external fixation system should be temporarily supported in the area where the strut is removed while this is being done.

Currently, in an effort to construct a temporary support during, for example, a strut-change-out procedure, health care providers may utilize a spare strut to temporarily support the frame. Alternatively, health care providers may use, for example, an external fixator or clamp. In use, the clamps may be coupled to the rings without utilizing one of the holes formed in the rings (e.g., clamps may clip onto the first and second rings via, for example, a press-fit connection). However, these clamps are not designed for long-term use within an external fixation system.

In addition, and/or alternatively, external fixation systems are often used for patients with complicated bone and soft tissue injuries/disorders. As such, external fixation systems may be used to stabilize bone segments while other injuries such as, for example, open wounds are being treated. As a result, the placement of the struts on a hexapod external fixation system can limit or reduce a health care provider's access to the patient's anatomy requiring medical attention.

Thus, it would be beneficial to provide a kit and corresponding methods of use that is arranged and configured to, for example, convert a hexapod external fixation system into a static frame. By enabling conversion of an external fixation system between, for example, a hexapod external fixation system and a static frame, health care providers can easily adjust to changing conditions. For example, utilizing a kit and/or corresponding methods of use per the present disclosure, health care providers can convert a hexapod external fixation system to a static frame to provide increased visualization of the patient's anatomy during an X-ray procedure. In addition, and/or alternatively, the kit and corresponding methods of use may enable a health care provider to selectively enable dynamization of the external fixation system during, for example, the consolidation phase, or enable construction of a static frame in an easy and timely manner, or facilitate strut-change out, and/or temporarily stabilization of a frame to provide a health care provider with a larger working window.

It is with respect to these and other considerations that the present disclosure may be useful.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides a kit for use with an external fixation system. In use, the kit includes a plurality of articulating clamps for coupling a rod to one of the rings of an external fixation system. In use, the clamps include a body portion having a stem arranged and configured to be received within an opening formed in one of the rings. The clamps further include a clamp portion or assembly (used interchangeably herein) arranged and configured to engage a rod spanning the first and second rings. For example, the clamp portion may be arranged and configured to engage the rod in a snap-fit or friction fit connection or manner Thus arranged, the clamp may be directly coupled to one of the rings and the rod, the clamp enabling the position of the ring to be adjusted relative to the rod. In this manner, the kit (e.g., clamps) may be utilized to convert a hexapod external fixation system to a static frame. Alternatively, the kit (e.g., clamps) may be utilized to temporarily replace one or more of the struts in a hexapod external fixation system to create a larger working and/or visualization window. In another embodiment, the clamps and rods may be utilized from the outset to create a static frame quickly and easily.

In one embodiment, a method of converting a hexapod external fixation system to a static frame is disclosed. In use, the struts of a hexapod external fixation system may be removed and replaced with clamps and rods thereby converting the hexapod external fixation system into a static frame. For example, in one embodiment, clamps may be circumferentially coupled to the first and second rings as needed. The clamps may be coupled to the rings by inserting a stem portion of the clamp into holes, slots, or the like formed in the rings (the terms holes and slots being used interchangeably herein without the intent to limit). Thereafter, rods may be coupled and secured to the clamps. Finally, the existing struts in the hexapod external fixation system may be removed.

In one embodiment, a method of providing an enlarged visualization and/or working window is disclosed. In use, one or more struts of a hexapod external fixation system may be removed and replaced with one or more clamps and a rod thereby creating a larger working or visualization window. For example, in one embodiment, one or more clamps may be coupled to one or both of the first and second rings as needed. The clamps may be coupled to the rings by inserting a stem portion of the clamp into holes formed in the rings. Thereafter, one or more rods may be coupled and secured to the clamp(s). Finally, one or more existing struts in the hexapod external fixation system may be removed thereby providing an increased or enlarged visualization and/or working window.

In one embodiment, a method of constructing a static frame is disclosed. In use, the first and second rings of an external fixation system may be coupled to each other utilizing parallel rods coupled to one or both of the rings via an articulating clamp. Thus arranged, increased flexibility in positioning the rings relative to each other is rendered possible along with enabling easier and more efficient construction of the static frame. For example, in one embodiment, clamps may be coupled to one or both of the first and second rings as needed. The clamps may be coupled to the rings by inserting a stem portion of the clamp into holes formed in the rings. Thereafter, rods may be coupled and secured to the clamp(s) and/or ring thereby providing a more efficient static frame with increased flexibility in positioning the first and second rings relative to each other.

In one embodiment, a kit for use with an external fixation system to one of facilitate conversion of the external fixation system into a static frame, enable temporary removal of one or more struts from the external fixation system to provide a larger visualization or working window, or enable construction of a static frame is disclosed. In one embodiment, the kit comprises first and second rings, one or more rods, and one or more articulating clamps. The first and second rings are arranged and configured to be coupled to a patient's bone, the first and second rings being arranged and configured to be coupled to each other via a plurality of external adjustable length struts, each of the first and second rings including a plurality of openings formed therein. The one or more rods are arranged and configured to span between the first and second rings. The one or more articulating clamps are arranged and configured to couple one of the one or more rods to one of the first and second rings; wherein each of the one or more articulating clamps include a stem arranged and configured to be received within one of the openings formed in one of the first and second rings.

In one embodiment, each of the one or more articulating clamps are arranged and configured to engage the rod spanning between the first and second rings via a snap-fit or friction fit connection.

In one embodiment, at least one of the one or more articulating clamps includes a body portion and a clamp portion, the body portion including the stem arranged and configured to be received within the opening formed in one of the first and second rings, the clamp portion arranged and configured to engage the rod spanning the first and second rings.

In one embodiment, the clamp portion is arranged and configured to move relative to the body portion to enable a position of the connected ring to be adjusted relative to the rod spanning the first and second rings.

In one embodiment, the stem includes an externally threaded post arranged and configured to receive a threaded nut.

In one embodiment, the clamp portion includes first and second jaw members in facing arrangement, the first and second jaw members arranged and configured to receive the rod spanning the first and second rings.

In one embodiment, the clamp further includes a bolt including an externally threaded rod and an enlarged spherical head portion, the bolt arranged and configured to couple the clamp portion to the body portion while enabling the clamp portion to articulate relative to the body portion.

In one embodiment, the body portion includes a bore arranged and configured to at least partially receive the enlarged spherical head portion.

In one embodiment, the clamp further comprises a threaded nut, the externally threaded rod of the bolt passing through the first and second jaw members so that engagement of the threaded nut with the externally threaded rod of the bolt secures a position of the rod spanning between the first and second rings between the first and second jaw members.

In one embodiment, the clamp further comprises a set screw arranged and configured to interact with the enlarged spherical head portion so that tightening of the set screw fixes a position of the clamp portion relative to the body portion.

In one embodiment, the first and second jaw members are biased apart from each other via a spring disposed between the first and second jaw members.

In one embodiment, the clamp portion includes a hinged clamp assembly arranged and configured to engage the rod spanning the first and second rings, the hinged clamp assembly including first and second arms hingeably coupled to each other.

In one embodiment, the one or more articulating clamps include first and second articulating clamps, the first articulating clamp coupling a first end of the rod spanning between the first and second rings to the first ring, the second articulating clamp coupling a second end of the rod spanning between the first and second rings to the second ring.

In one embodiment, the one or more articulating clamps include a first articulating clamp coupling a first end of the rod spanning between the first and second rings to the first ring, a second end of the rod spanning between the first and second rings being coupled o the second ring via one or more threaded nuts.

In one embodiment, the kit further comprises one or more dynamization washers arranged and configured to be positioned between one of the one or more articulating clamps and one of the first and second rings, the dynamization washer arranged and configured to enable micro-motion of the clamp to the ring.

In one embodiment, the one or more dynamization washers include an opening passing therethrough arranged and configured to enable the stem of the articulating clamp to pass therethrough, the dynamization washer including a containment cup and a damper, the containment cup including an outer ledge defining a pocket for receiving at least a portion of the damper therein, the damper being arranged and configured to compress to enable micro-motion of the articulating clamp relative to the ring.

In one embodiment, a method is disclosed. The method comprises inserting a stem of an articulating clamp through an opening formed a first ring of an external fixation system; coupling one end of a rod to the articulating clamp, the rod spanning a distance between the first ring of the external fixation system and a second ring of the external fixation system; adjusting a portion of the articulating clamp relative to the first ring as needed; and removing one or more adjustable length struts extending between the first and second rings.

Embodiments of the present disclosure provide numerous advantages. For example, the kit (e.g., clamps) and corresponding methods of use enable constructing a static frame quickly and with increased flexibility (e.g., a static frame with increased options when constructing the static frame). In addition, the kit (e.g., clamps) and corresponding methods of use enable a health care provider to convert a hexapod external fixation system to a static frame as desired and/or to temporarily support first and second rings while one or more struts are temporarily removed to provide an increased working and/or visualization window.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
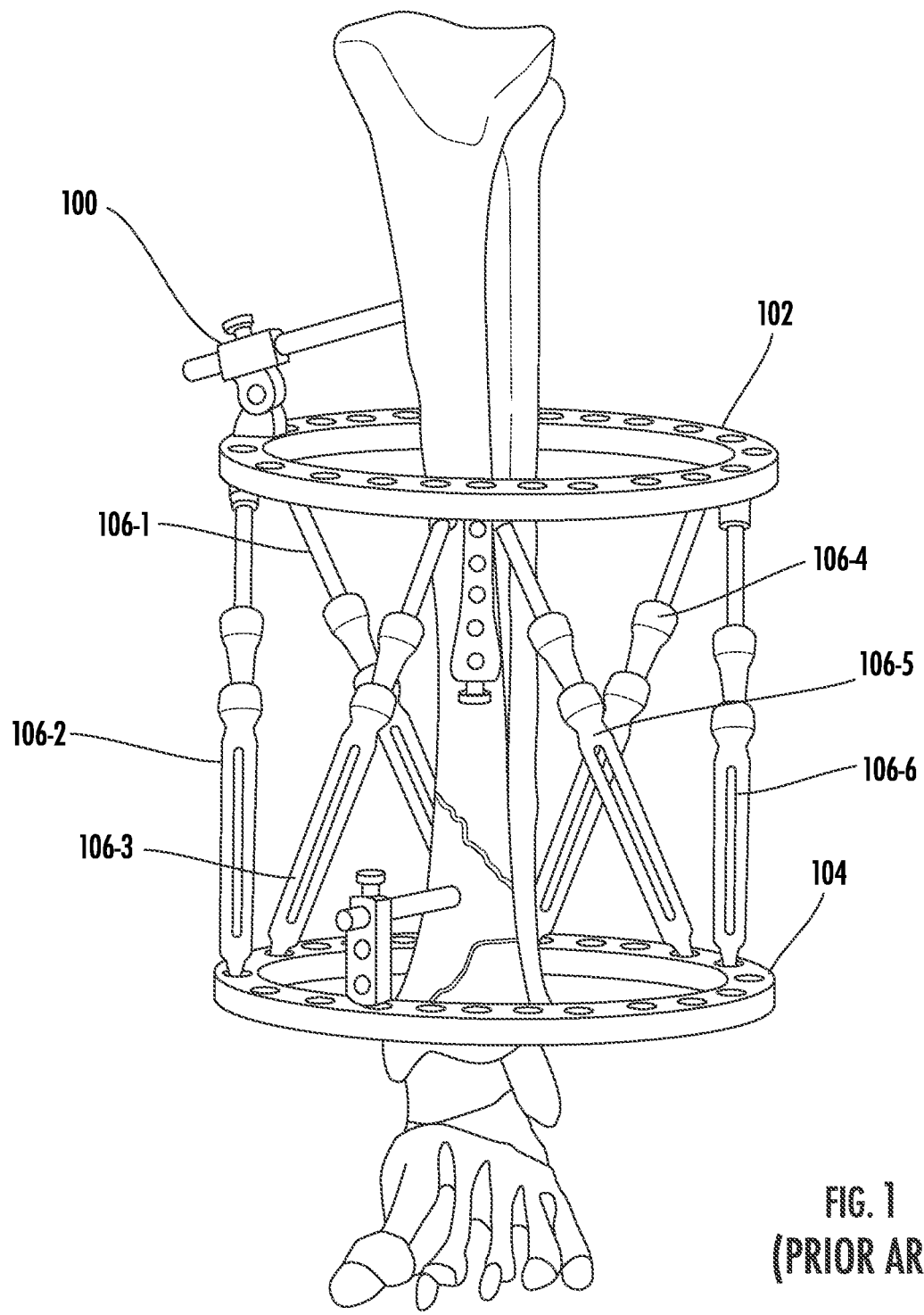
FIG. 1 illustrates an example embodiment of a known hexapod external fixation system.

The drawings are not necessarily to scale. The drawings are merely representations, not intended to portray specific parameters of the disclosure. The drawings are intended to depict various embodiments of the disclosure, and therefore are not be considered as limiting in scope. In the drawings, like numbering represents like elements throughout unless otherwise noted.

DETAILED DESCRIPTION

Various features or the like of a kit, components thereof, and corresponding methods of use with an external fixation system will now be described more fully herein with reference to the accompanying drawings, in which one or more features of the kit, components, and corresponding methods of use will be shown and described. It should be appreciated that the various features or the like may be used independently of, or in combination, with each other. It will be appreciated that a kit, components, and corresponding methods of use as disclosed herein may be embodied in many different forms and may selectively include one or more concepts, features, or functions described herein. As such, the kit, components, and corresponding methods of use should not be construed as being limited to the specific embodiments set forth herein. Rather, these embodiments are provided so that this disclosure will convey certain features of the kit, components, and corresponding methods of use to those skilled in the art.

As will be described in greater detail, in use, the kit or conversion kit (used interchangeably herein without the intent to limit) includes a system of external fixators or clamps (used interchangeably herein without the intent to limit). In use, the clamps are arranged and configured to couple, engage, attach, etc. (used interchangeably herein without the intent to limit) directly to the rings of an external fixation system. More specifically, the clamps are arranged and configured to engage the rings utilizing one of the holes formed in the rings. In addition, the clamps are arranged and configured to receive a rod such as, for example, a threaded rod, a non-threaded rod, a carbon fiber rod, etc., that spans the distance between the first and second rings of the external fixation system.

In use, in one embodiment, first and second clamps are coupled to first and second rings, respectively. Thereafter, a rod may be coupled to the first and second clamps. Alternatively, a single clamp may be coupled to a first end of the rod to couple the rod to a first ring while the second end of the rod may be coupled to the second ring by any other suitable mechanism such as, for example, threaded nuts.

In either event, in accordance with one or more features of the present disclosure, the kit is arranged and configured to enable the hexapod external fixation system to be quickly and easily converted to a static frame. For example, in one embodiment, the struts may be removed and replaced with clamps and rods thereby converting the hexapod external fixation system into a static frame. Alternatively, one or more struts may be removed and replaced with one or more clamps and a rod thereby, for example, creating a larger working or visualization window. In another embodiment, the clamps and rods may be utilized from the outset to create a static frame quickly and easily. For example, in one embodiment, the first and second rings may be coupled to each other utilizing parallel rods coupled to one or both of the rings via an articulating clamp. Thus arranged, the clamps are arranged and configured to quickly and easily engage the rings of the external fixation system and quickly and easily engage the rod. In addition, the clamps are arranged and configured to enable increased flexibility, movement, articulation, rotation, etc. (terms used interchangeably without the intent to limit) in positioning the rings relative to each other.

Figure 2A:
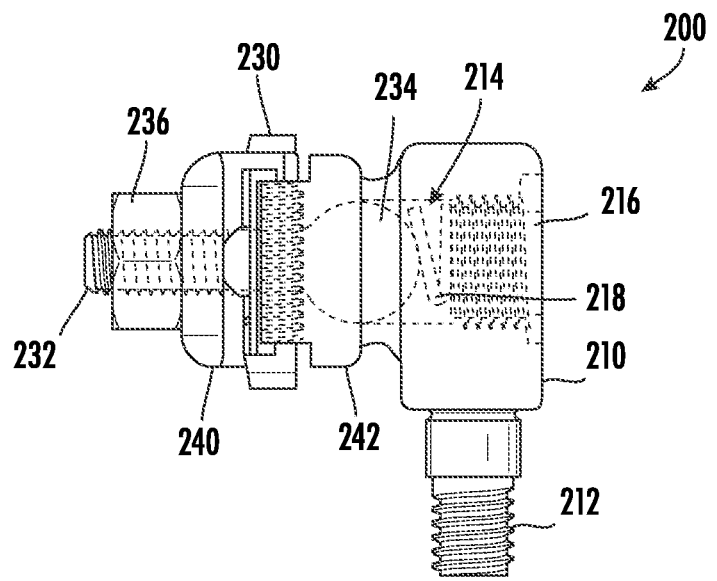
FIG. 2A illustrates a side view of an example of an embodiment of a clamp that may be used in an external fixation system in accordance with one feature of the present disclosure.
Figure 2B:
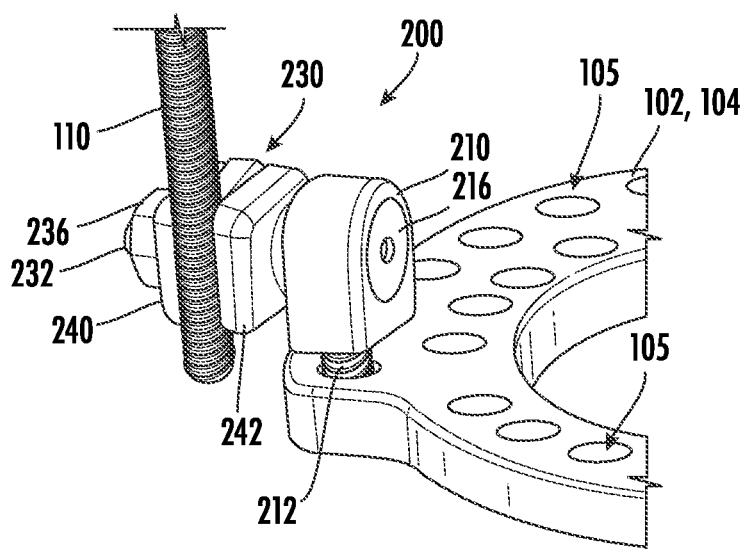
FIG. 2B illustrates a perspective view of the clamp shown in FIG. 2A coupled to a ring of an external fixation system in accordance with one feature of the present disclosure.

Referring to FIGS. 2A and 2B, in accordance with one or more features of the present disclosure, an example embodiment of a clamp 200 is shown. As shown, the clamp 200 includes a body portion 210 and a clamp portion 230. In the example embodiment, the body portion 210 includes a stem component (e.g., a male threaded post) 212 arranged and configured to be received within an opening 105 formed in one of the first and second rings 102, 104 (shown as the second ring 104) for securing the clamp 200 to one of the rings 102, 104 utilizing, for example, a threaded nut (not shown). That is, as illustrated, the stem component 212 may include external threads so that once positioned within an opening 105 formed in one of the rings 102, 104, the clamp 200 can be engaged to the ring 102, 104 via, for example, a threaded nut (e.g., the exposed portion of the stem component 212 can be threadably coupled to a ring 102, 104 via a threaded nut), although other fastening mechanisms are envisioned.

In addition, the clamp portion 230 of the clamp 200 is arranged and configured to engage a rod 110 for spanning the distance between the rings 102, 104. That is, as illustrated, the clamp portion 230 includes first and second jaw members 240, 242 in facing arrangement. Thus arranged, in use, the first and second jaw members 240, 242 are arranged and configured to receive, engage, etc. the rod 110 spanning the distance between the first and second rings 102, 104.

As illustrated, the clamp 200 also includes a locking ball joint design between the clamp portion 230 and the body portion 210. In use, the locking ball joint design is arranged and configured to enable the clamp portion 230 to move, rotate, articulate, etc. relative to the body portion 210 to enable increased flexibility between the positioning of the clamp portion 230, and hence the rod 110, relative to the body portion 210, and hence the rings 102, 104. That is, as illustrated in the example embodiment, the clamp portion 230 includes a threaded bolt 232 having an enlarged spherical head 234, the enlarged spherical head 234 being in contact, received in, etc. a bore 214 (e.g., a spherically-shaped portion or surface of the bore 214 for contacting with the spherical head 234) formed in the body portion 210 of the clamp 200. Thus arranged, the threaded bolt 232, and hence the clamp portion 230, can articulate relative to the body portion 210. The clamp 200 may also include a threaded nut 236 for engaging an end of the threaded bolt 232 opposite the enlarged spherical head 234. In use, rotation of the threaded nut 236 secures a position of the rod 110 within the clamp assembly (e.g., between the first and second jaw members 240, 242). That is, in use, tightening of the threaded nut 236 compresses the first jaw 240 against the second jaw 242 to thereby secure a position of the rod 110 between the first and second jaw members 240, 242.

In one embodiment, the first jaw member 240 may be arranged and configured to translate along a direction perpendicular to a longitudinal length of the threaded bolt 232. The second jaw member 242 may be arranged and configured to engage the threaded bolt 232 via a keyway that engages a key on a shaft of the threaded bolt 232, which acts to keep the second jaw member 242 from rotating relative to the threaded bolt 232 once the clamp portion 230 is tightened (the bolt 232 can rotate relative to the first and second jaws 240, 242 prior to being tightened). A spring housed within the clamp portion 230 between the first jaw member 240 and the second jaw member 232 biases the jaw members 230, 232 to maintain their alignment unless a user applies a force to the first jaw member 240 to push against the spring. Thus arranged, in use, a health care provider can quickly secure (e.g., snap) the rod 110 into position from a side of the clamp assembly rather than, for example, having to thread the rod 110 through the clamp assembly.

As illustrated, in one embodiment, the rod 110 is a threaded rod and the first and second jaw members 240, 242 are arranged and configured to engage the threaded rod 110 to firmly secure a position of the threaded rod 110 within the clamp assembly. For example, an inner surface of the first and second jaw members 240, 242 may include a plurality of threads, ridges, serrations, or the like, for engaging the outer surface of the threaded rod 110. However, it should be appreciated that the rod 110 may be any suitable rod now known or hereafter developed for spanning the distance between the first and second rings 102, 104. For example, the rod 110 may be threaded or non-threaded and may be manufactured from metal, carbon-fiber, etc. The rod 110 may have any size. For example, in one embodiment, the rod 110 may have a diameter of 6 mm, although other diameters may be used.

In addition, the body portion 210 may include a set screw 216 in communication with the bore 214 for interacting with the enlarged spherical head 234. For example, as shown, a spring 218 may be positioned between the set screw 216 and the enlarged spherical head 234 of the threaded bolt 232. In use, rotation of the set screw 216 compresses the enlarged spherical head 234 against an inner surface of the bore 214 to secure a position of the threaded bolt 232 relative to the body portion 210, thus securing a position of the clamp portion 230 relative to the body portion 210.

Thus arranged, in accordance with one or more features of the present disclosure and as will be shown, the clamp 200 enables more degrees of freedom as compared to directly coupling rods to the rings 102, 104 via nuts and/or rods utilizing conical washers. In addition, the clamps 200 simultaneously provide a quicker and easier engagement to the rings 102, 104 and the rod 110. In addition, the additional freedom provided enables the clamps 200 to be configured in any number of configurations, which provides health care providers with additional options when working around other existing hardware.

Figure 3:
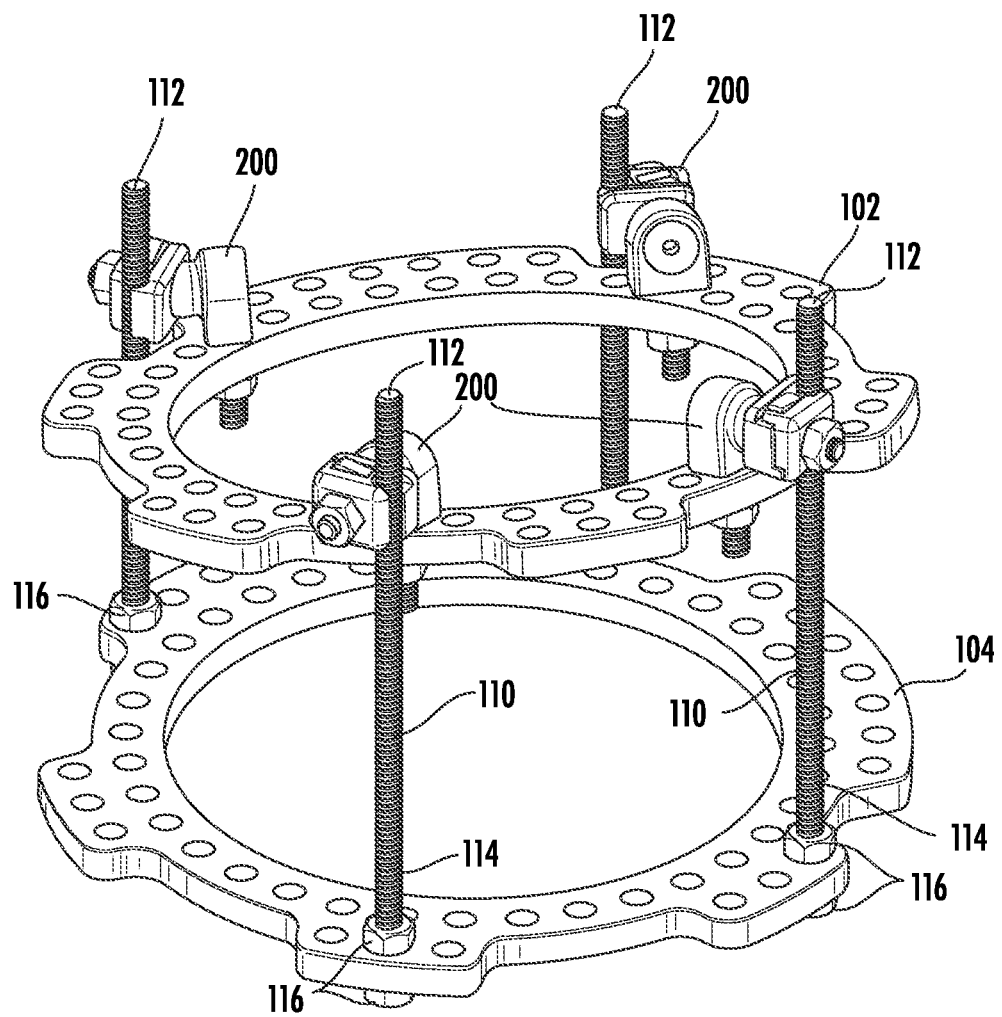
FIG. 3 illustrates a perspective view of the clamps shown in FIGS. 2A and 2B used to construct an example of an embodiment of a static frame.
Figure 4:
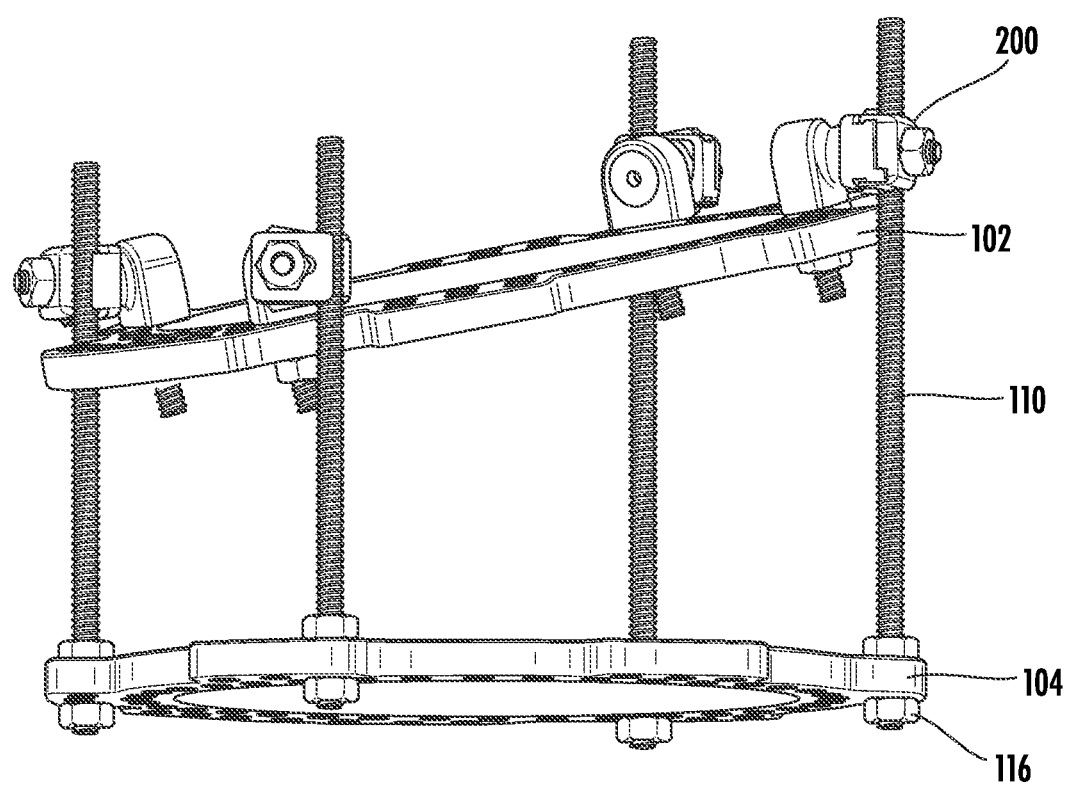
FIG. 4 illustrates a side view of the clamps and static frame shown in FIG. 3, the clamps enabling increased angulation of the rings relative to each other.
Figure 5A:
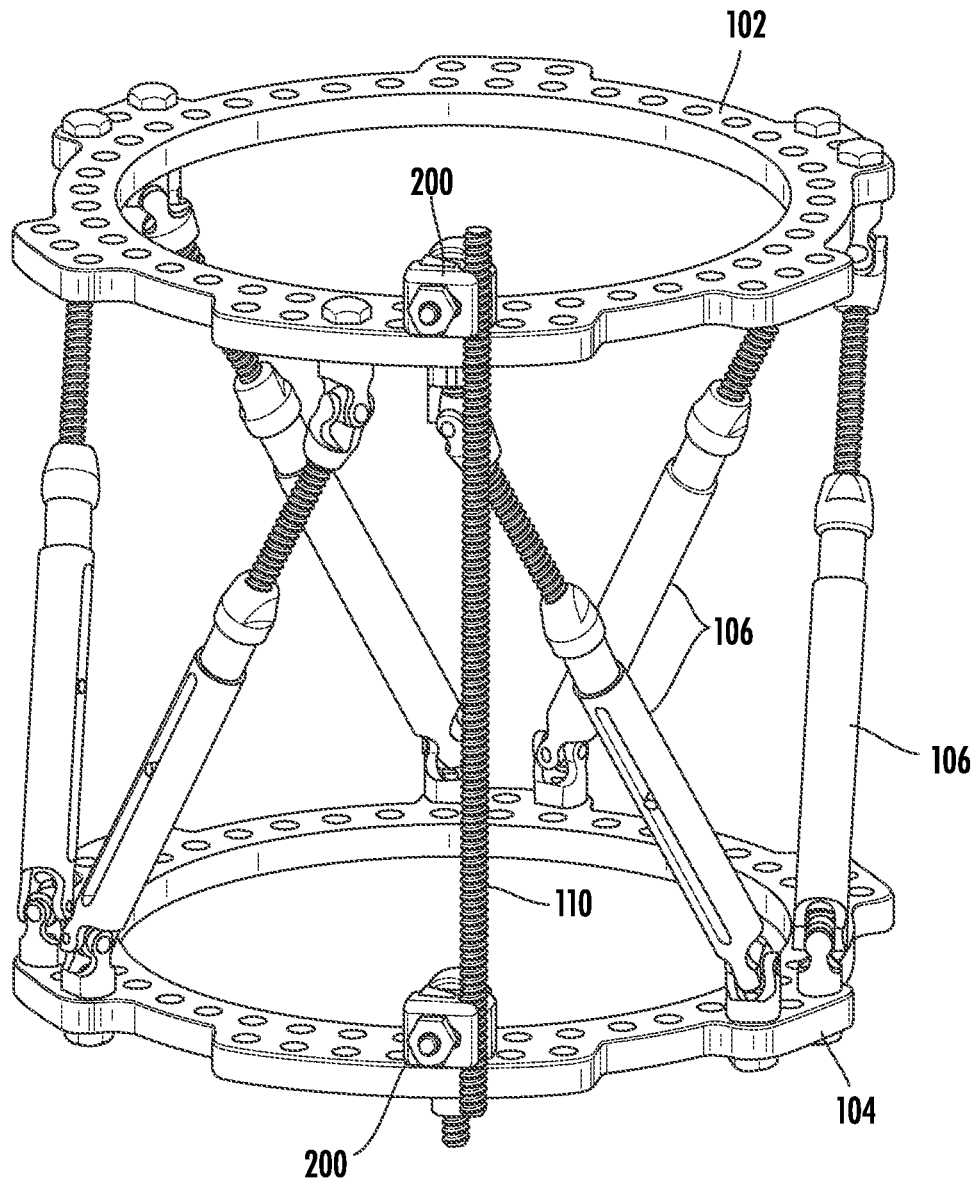
FIG. 5A illustrates a perspective view of the clamp shown in FIG. 2A coupled to the rings of a hexapod external fixation system in accordance with one feature of the present disclosure.
Figure 5B:
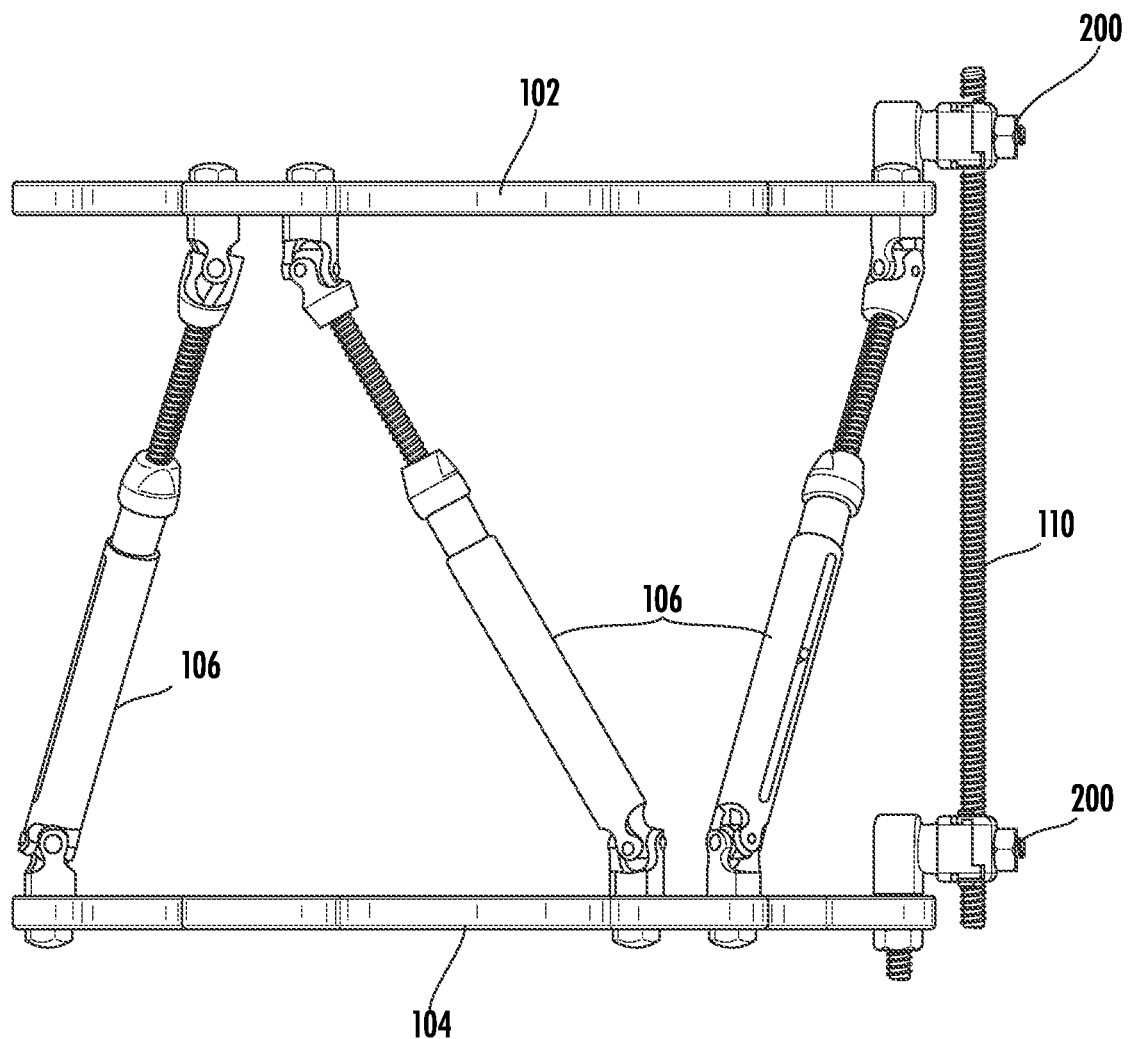
FIG. 5B illustrates a side view of hexapod external fixation system shown in FIG.
Figure 6:
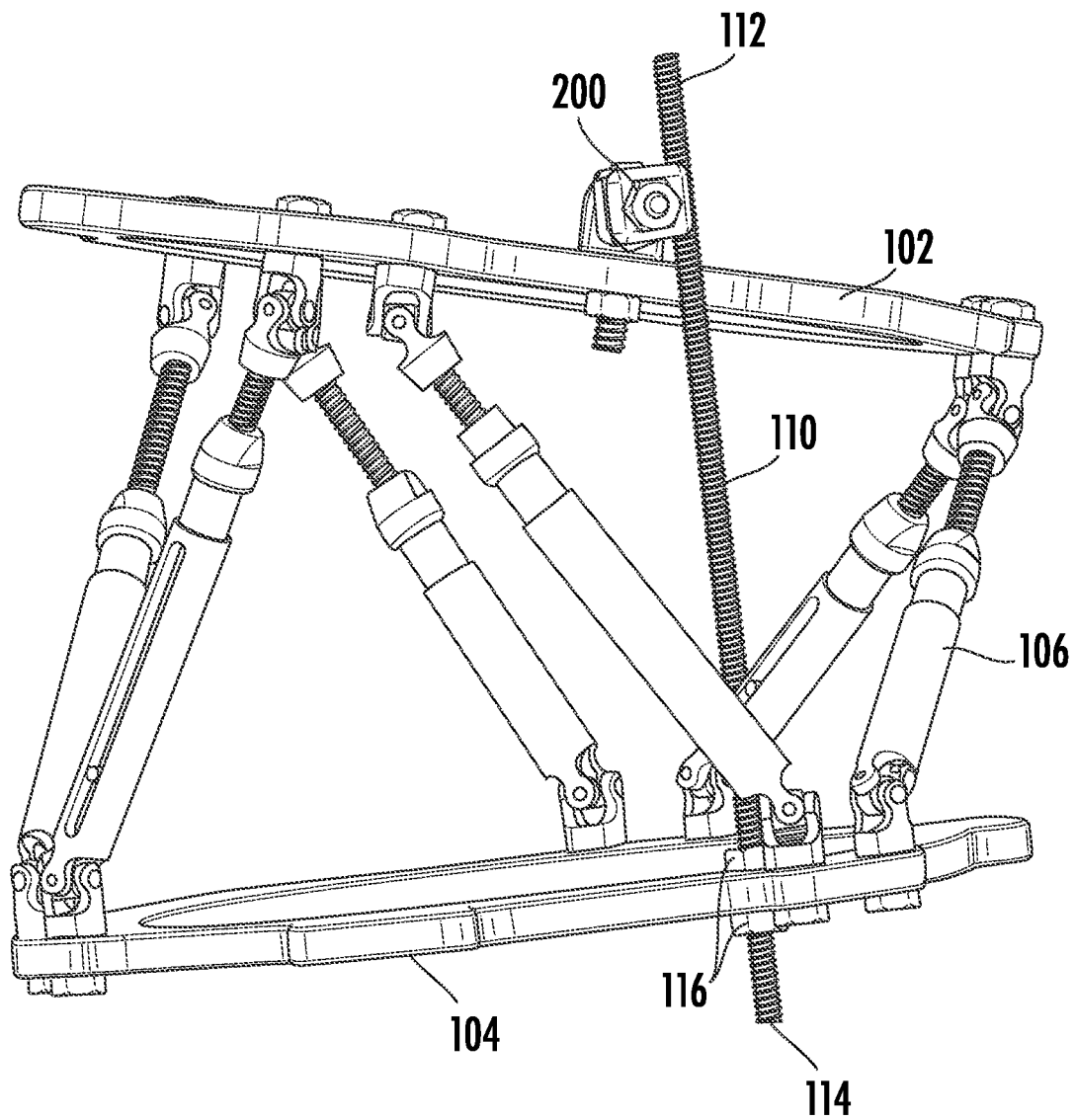
FIG. 6 illustrates a perspective view of the clamp shown in FIG. 2A coupled to a ring of a hexapod external fixation system in accordance with one feature of the present disclosure, the clamp illustrated enabling increased angulation of the rings relative to each other.

In use, the clamps 200 may be used in pairs to couple each end of a rod 110 to the first and second rings 102, 104 (as generally shown in FIGS. 5A and 5B). Alternatively, the clamps 200 may be used on only one side of the frame to couple one end of the rod to one of the first and second rings 102, 104 while the other end of the rod 110 may be coupled using other suitable mechanisms such as, for example, threaded nuts (as generally shown in FIGS. 3, 4, and 6). For example, referring to FIG. 3, clamps 200 may be used to couple a first end 112 of the rod 110 (e.g., threaded rod) to the first ring 102 while first and second nuts 116 may be used to couple a second end 114 of the rod 110 to the second ring 104. Thus arranged, a static frame may be quickly and easily constructed. Alternatively, the clamps 200 may be used on both sides of the frame to couple both the first and second ends 112, 114 of the rod 110 to the first and second rings 102, 104, respectively. While four rods 110 are shown, it should be appreciated that any number of rods may be utilized including, for example, three, five, six, or more.

Referring to FIG. 4, incorporation of the clamps 200 to couple the rod 110 to one or both of the rings (shown as first ring 102) enables increased angulation of the rings 102, 104 relative to each other. For example, as illustrated, it has been found that by utilizing articulating clamps, each of the rings 102, 104 may be angulated by ±30 degrees of parallel, this is in contrast with known prior art devices that only provide ±14 degrees of angulation.

Referring to FIGS. 5A and 5B, an example of an embodiment of one or more clamps 200 being used in conjunction with a hexapod external fixation system is illustrated. As illustrated, and as previously mentioned, in a hexapod external fixation system, the first and second rings 102, 104 may be connected by six adjustable length struts 106. Given the orientation, size, etc. of the struts, visualization of the patient's underlying bone and/or working access to the patient's underlying anatomy may be compromised. In connection with one feature of the present disclosure, one or more clamps 200 and one or more rods 110 may be used to couple the first and second rings 102, 104 during, for example, an operation. Subsequently, one or more of the adjustable struts 106 may be removed. Thus arranged, a larger visualization or working window may be created while maintaining the integrity of the frame in a quick and easy manner.

As previously mentioned in connection with constructing a static frame, in use, the clamps 200 may be used in pairs to couple each end of a rod 110 to the first and second rings 102, 104. Alternatively, referring to FIG. 6, the clamps 200 may be used on only one side of the frame to couple one end of the rod to one of the first and second rings 102, 104 while the other end of the rod 110 may be coupled using other suitable mechanisms such as, for example, threaded nuts. For example, as illustrated, clamp 200 may be used to couple a first end 112 of the rod 110 (e.g., threaded rod) to the first ring 102 while first and second nuts 116 may be used to couple a second end 114 of the rod 110 to the second ring 104. In addition, as illustrated, incorporation of one or more clamps 200 to couple the rod 110 to one or both of the rings (shown as first ring 102) enables increased angulation of the rings relative to the rod 110. For example, as illustrated, by utilizing articulating clamps, it has been found that each of the rings may be angulated by ±30 degrees of parallel, this is in contrast with known prior art devices that only provide ±14 degrees of angulation. Thus arranged, easier and more efficient construction of a static frame is enabled.

Figure 7A:
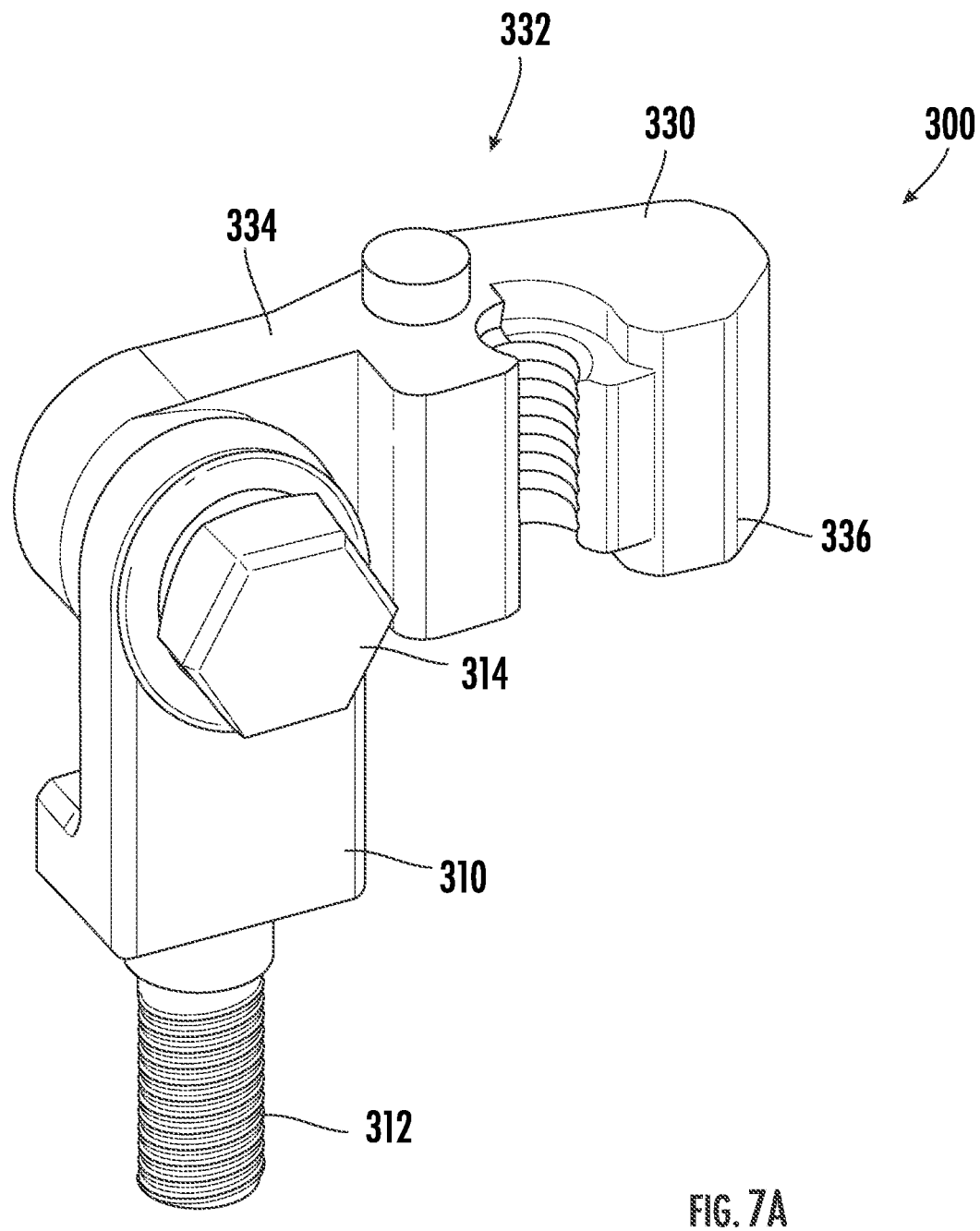
FIG. 7A illustrates a perspective view of an alternate example of an embodiment of a clamp that may be used in an external fixation system in accordance with one feature of the present disclosure.
Figure 7B:
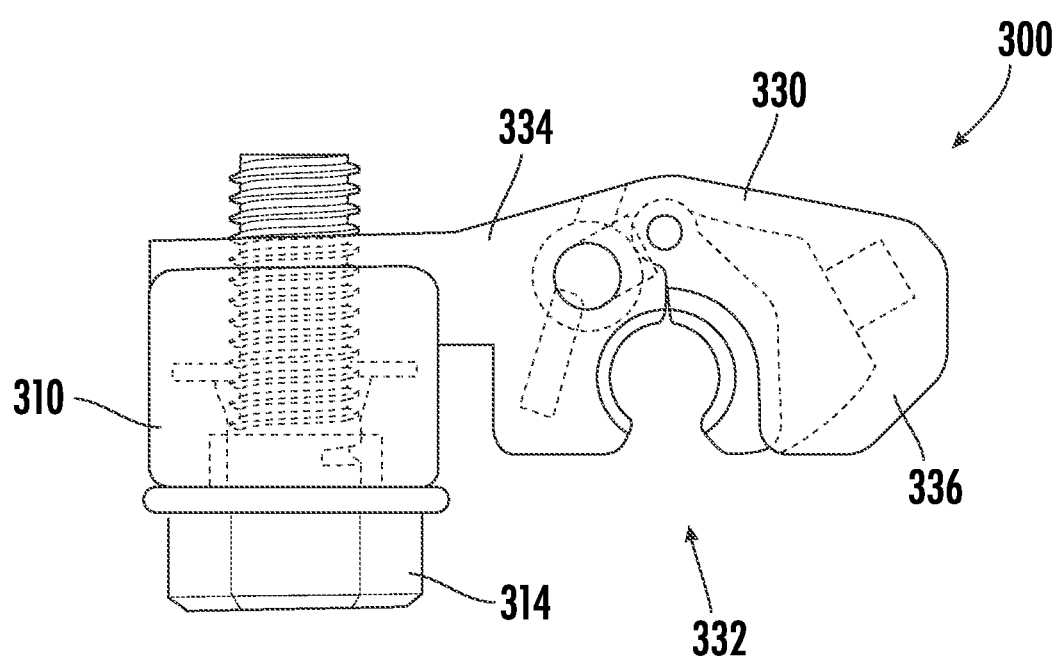
FIG. 7B illustrates a top view of the clamp shown in FIG. 7A.

While an example embodiment of a clamp is shown and described in connection with FIGS. 2A-6, it should be appreciated that other versions of clamps may be utilized. For example, referring to FIGS. 7A and 7B, a side opening clamp 300 may be utilized. As illustrated, the clamp 300 includes a body portion 310 having a stem component (e.g., a male threaded post) 312 arranged and configured to be received within an opening 105 formed in one of the rings 102, 104 for securing the clamp 300 to the ring 102, 104. In addition, the clamp 300 includes a clamp portion 330 incorporating a hinged or a cam clamp assembly 332 arranged and configured to engage a rod 110. The clamp 300 may also include a threaded bolt and nut 314 for coupling the clamp portion 330 to the body portion 310. In addition, the clamp portion 330 may be coupled to the body portion 310 via a poker chip design (e.g., intercoupling serrations or ridges) to secure an angle of the clamp portion 330 relative to the body portion 310. In use, by coupling the clamp portion 330 to the body portion 310 via a threaded bolt and nut 314, the clamp portion 330 may be rotated, articulate, etc. relative to the body portion 310 for providing increased flexibility in positioning the rings 102, 104 relative to the rod 110 spanning the first and second rings 102, 104.

In use, similar to clamp 200 previously described and illustrated, the stem component 312 of the clamp 300 is arranged and configured to be received within an opening 105 formed in one of the first and second rings 102, 104. The stem component 312 may include external threads so that once positioned within the opening 105 formed in the ring 102, 104, the clamp 300 can be engaged to the ring 102, 104 via, for example, a threaded nut (not shown).

In the example embodiment, the clamp portion 330 includes a hinged clamp assembly 332 arranged and configured to couple, close around, or the like, the rod 110. In one embodiment, the clamp assembly 332 includes a first arm 334 and a second arm 336 hingeably coupled to the first arm 334. In one embodiment, the clamp assembly 332 (e.g., the first and second arms 334, 336) may be arranged and configured to be biased to a closed configuration as illustrated so that, in use, the rod 110 may be snap-fitted within the opening formed in the clamp assembly 332.

Figure 8:
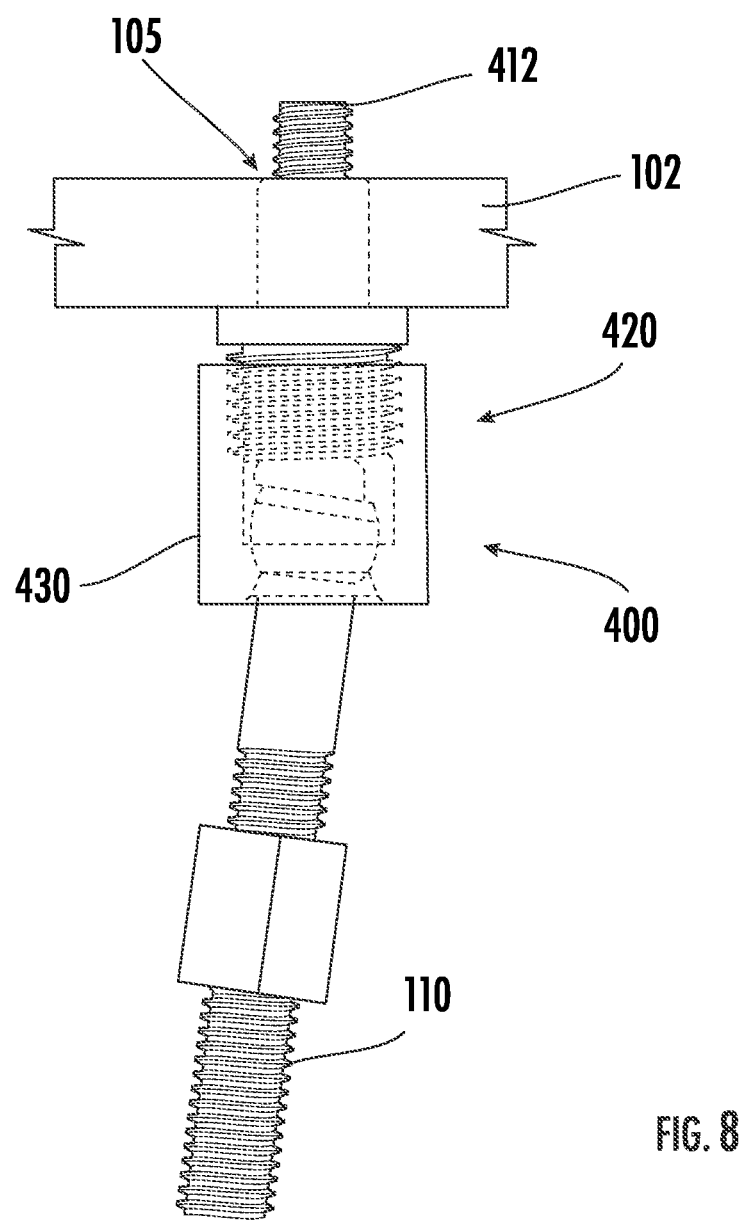
FIG. 8 illustrates a side view of an alternate example of an embodiment of a clamp that may be used in an external fixation system in accordance with one feature of the present disclosure.

Alternatively, referring to FIG. 8, in an alternate example embodiment, the clamp 400 may be in the form of a lockable ball joint or universal joint between the rings 102, 104. In use, the clamp 400 includes a threaded stem component 412 for engaging one of the openings 105 formed in one of the first and second rings 102, 104. The rod 110 being coupled the stem component 412 via a lockable ball joint or universal joint 420 positioned between the rod 110 (e.g., an end portion of the rod 110 and the stem component 412). An outer sleeve 430 may be threaded thereby securing a position of the lockable ball joint or universal joint 420.

It should be appreciated that while several example embodiments of clamps have been shown and described, in use, any suitable clamp now known or hereafter developed may be used. As such, the present disclosure is not limited to any particular type of clamp unless explicitly claimed.

Figure 9A:
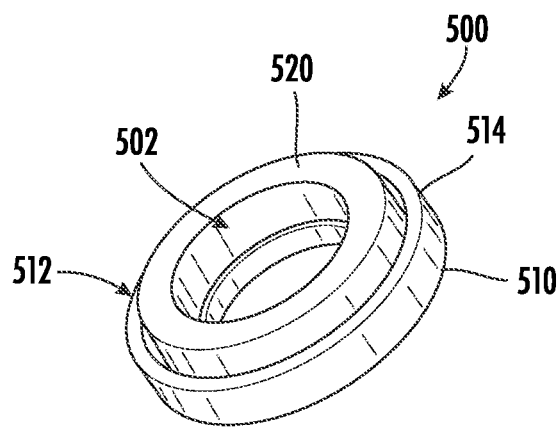
FIG. 9A illustrates a perspective view of an example of an embodiment of a dynamization washer that may be used in connection with an external fixation system in accordance with one or more features of the present disclosure.
Figure 9B:
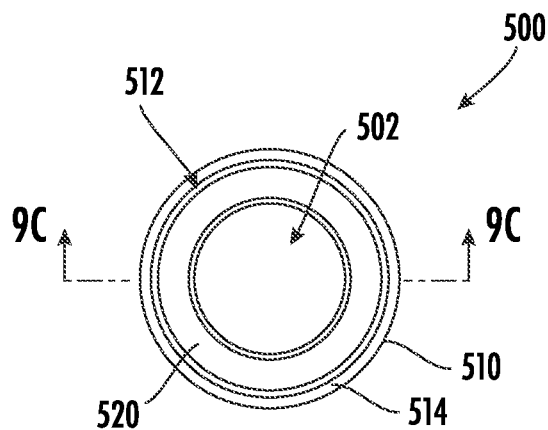
FIG. 9B illustrates a top view of the dynamization washer shown in FIG. 9A.
Figure 9C:
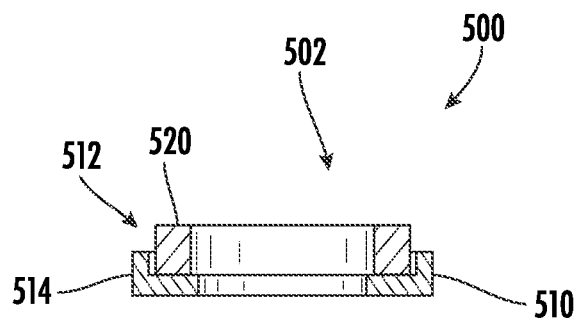
FIG. 9C illustrates a cross-sectional view of the dynamization washer shown in FIGS. 9A and 9B, the cross-sectional view taken along line 9C-9C in FIG. 9B.

Referring to FIGS. 9A-9C, in accordance with another feature of the present disclosure, an example embodiment of a dynamization washer or mechanism 500 (terms used interchangeably herein without the intent to limit) is illustrated. In use, the washer 500 may be positioned between the clamp such as, for example, clamp 200, clamp 300, clamp 400, or the like, and the ring 102, 104. Incorporation of the dynamization washer 500 enables dynamization or micromotion of the clamp 200, 300, 400 relative to the ring 102, 104 (e.g., controlled axial motion between the clamp 200, 300, 400, and hence the rod 110 coupled thereto, and the corresponding rings 102, 104).

As shown, the dynamization washer 500 includes a containment cup 510 and a damper 520. In use, the dynamization washer 500 is positioned between the ring 102, 104 and the clamp 200, 300, 400. The dynamization washer 500 may be coupled to the ring 102, 104 and the clamp 200, 300, 400 via for example the stem component 212, 312, 412 used to couple the clamp 200, 300, 400 to the ring 102, 104, the stem component 212, 312, 412 passing thru an opening 502 formed in the dynamization washer 500.

As shown, the containment cup 510 and the damper 520 may have corresponding circular shapes, although other suitable shapes are envisioned. In use, the containment cup 510 may include a pocket 512 defined by, for example, a ledge 514 projecting along an outer circumference thereof. The pocket 512 being arranged and configured to receive at least a portion of the damper 520. In one embodiment, the containment cup 510 may be made from a substantially rigid material such as, for example, a metal such as stainless steel, titanium, etc. The damper 520 may be manufactured from a softer, compressible material such as, for example, a silicone, rubber, elastomer, etc. Thus arranged, in use, the damper 520 can be compressed thus facilitating axial compression of the clamp 200, 300, 400 relative to the ring 102, 104 during, for example, a patient walking. As will be appreciated by one of ordinary skill in the art, by controlling the extent by which the damper 520 extends beyond the ledge 514 of the containment cup 510, one can control the amount of compression and thus axial movement. That is, the extent or distance that the damper 520 extends beyond the containment cup 510 dictates the amount of axial movement provided.

Although a particular example of a dynamization washer has been shown and described, it is envisioned that other suitable mechanisms may be utilized. For example, in one embodiment, it is envisioned that dynamization may be built into the clamp. In addition, it is envisioned that dynamization may be selectively lockable so that a health care provider can elect to enable dynamization in one clamp but not another. In addition, it is envisioned that the amount of dynamization enabled may be selectable, incrementable, etc. For example, a health care provider could initially elect to not allow any dynamization. Thereafter, the health care provider could enable 0.5 mm of dynamization followed by, for example, 1 mm, 1.5 mm, etc. of dynamization.

Although a particular external fixation system has been shown and described, it should be appreciated that the present disclosure can be used in conjunction with any now known or hereafter developed external fixation system. For example, it is envisioned that the kit can be used with any now known or hereafter developed rings. For example, while the clamps have been shown and described as mating (e.g., being received within) a hole formed through the rings, it is envisioned that the clamps could be modified to mate with openings that extend from a side surface of the rings (e.g., holes may be arranged and configured on the outside surface or face of the ring).

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations. Moreover, the following claims are hereby incorporated into this Detailed Description by this reference, with each claim standing on its own as a separate embodiment of the present disclosure.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

What is claimed is:

1. A kit for use with an external fixation system to one of facilitate conversion of the external fixation system into a static frame, enable temporary removal of one or more struts from the external fixation system to provide a larger visualization or working window, or enable construction of a static frame, the kit comprising:
   first and second rings arranged and configured to be coupled to a patient's bone, the first and second rings being arranged and configured to be coupled to each other via a plurality of external adjustable length struts, each of the first and second rings including a plurality of openings formed therein;
   one or more rods arranged and configured to span between the first and second rings; and
   one or more articulating clamps arranged and configured to couple one of the one or more rods to one of the first and second rings;
   wherein each of the one or more articulating clamps include a stem arranged and configured to be received within one of the openings formed in one of the first and second rings; and
   wherein each of the one or more articulating clamps are arranged and configured to engage the rod spanning between the first and second rings via a snap-fit or friction fit connection; at least one of the one or more articulating clamps includes a body portion and a clamp portion, the body portion including the stem arranged and configured to be received within the opening formed in one of the first and second rings, the clamp portion arranged and configured to engage the rod spanning the first and second rings, the clamp portion includes first and second jaw members in facing arrangement, the first and second jaw members arranged and configured to receive the rod spanning the first and second rings, and the clamp further includes a bolt including an externally threaded rod and an enlarged spherical head portion, the bolt arranged and configured to couple the clamp portion to the body portion while enabling the clamp portion to articulate relative to the body portion.

2. The kit according to claim 1, wherein the clamp portion is arranged and configured to move relative to the body portion to enable a position of the connected ring to be adjusted relative to the rod spanning the first and second rings.

3. The kit according to claim 1, wherein the stem includes an externally threaded post arranged and configured to receive a threaded nut.

4. The kit according to claim 1, wherein the body portion includes a bore arranged and configured to at least partially receive the enlarged spherical head portion.

5. The kit according to claim 1, wherein the clamp further comprises a threaded nut, the externally threaded rod of the bolt passing through the first and second jaw members so that engagement of the threaded nut with the externally threaded rod of the bolt secures a position of the rod spanning between the first and second rings between the first and second jaw members.

6. The kit according to claim 1, wherein the clamp further comprises a set screw arranged and configured to interact with the enlarged spherical head portion so that tightening of the set screw fixes a position of the clamp portion relative to the body portion.

7. The kit according to claim 1, wherein the first and second jaw members are biased apart from each other via a spring disposed between the first and second jaw members.

8. The kit according to claim 1, wherein the clamp portion includes a hinged clamp assembly arranged and configured to engage the rod spanning the first and second rings, the hinged clamp assembly including first and second arms hingeably coupled to each other.

9. The kit according to claim 1, wherein the one or more articulating clamps include first and second articulating clamps, the first articulating clamp coupling a first end of the rod spanning between the first and second rings to the first ring, the second articulating clamp coupling a second end of the rod spanning between the first and second rings to the second ring.

10. The kit according to claim 1, wherein the one or more articulating clamps include a first articulating clamp coupling a first end of the rod spanning between the first and second rings to the first ring, a second end of the rod spanning between the first and second rings being coupled o the second ring via one or more threaded nuts.

11. The kit according to claim 1, further comprising one or more dynamization washers arranged and configured to be positioned between one of the one or more articulating clamps and one of the first and second rings, the dynamization washer arranged and configured to enable micro-motion of the clamp to the ring.

12. The kit according to claim 11, wherein the one or more dynamization washers include an opening passing therethrough arranged and configured to enable the stem of the articulating clamp to pass therethrough, the dynamization washer including a containment cup and a damper, the containment cup including an outer ledge defining a pocket for receiving at least a portion of the damper therein, the damper being arranged and configured to compress to enable micro-motion of the articulating clamp relative to the ring.

13. A kit for use with an external fixation system to one of facilitate conversion of the external fixation system into a static frame, enable temporary removal of one or more struts from the external fixation system to provide a larger visualization or working window, or enable construction of a static frame, the kit comprising:
    first and second rings arranged and configured to be coupled to a patient's bone, the first and second rings being arranged and configured to be coupled to each other via a plurality of external adjustable length struts, each of the first and second rings including a plurality of openings formed therein;
    one or more rods arranged and configured to span between the first and second rings; and
    one or more articulating clamps arranged and configured to couple one of the one or more rods to one of the first and second rings;
    wherein each of the one or more articulating clamps include a stem arranged and configured to be received within one of the openings formed in one of the first and second rings; and
    wherein each of the one or more articulating clamps are arranged and configured to engage the rod spanning between the first and second rings via a snap-fit or friction fit connection, at least one of the one or more articulating clamps includes a body portion and a clamp portion, the body portion including the stem arranged and configured to be received within the opening formed in one of the first and second rings, the clamp portion arranged and configured to engage the rod spanning the first and second rings, the clamp portion includes first and second jaw members in facing arrangement, the first and second jaw members arranged and configured to receive the rod spanning the first and second rings, and
    wherein the first and second jaw members are biased apart from each other via a spring disposed between the first and second jaw members.

14. The kit according to claim 13, wherein the clamp portion is arranged and configured to move relative to the body portion to enable a position of the connected ring to be adjusted relative to the rod spanning the first and second rings.

15. The kit according to claim 13, wherein the stem includes an externally threaded post arranged and configured to receive a threaded nut.

16. The kit according to claim 13, wherein the clamp further includes a bolt including an externally threaded rod and an enlarged spherical head portion, the body portion includes a bore arranged and configured to at least partially receive the enlarged spherical head portion, the bolt is arranged and configured to couple the clamp portion to the body portion while enabling the clamp portion to articulate relative to the body portion.

17. The kit according to claim 16, wherein the clamp further comprises a threaded nut, the externally threaded rod of the bolt passing through the first and second jaw members so that engagement of the threaded nut with the externally threaded rod of the bolt secures a position of the rod spanning between the first and second rings between the first and second jaw members.

18. The kit according to claim 16, wherein the clamp further comprises a set screw arranged and configured to interact with the enlarged spherical head portion so that tightening of the set screw fixes a position of the clamp portion relative to the body portion.

19. The kit according to claim 13, further comprising one or more dynamization washers arranged and configured to be positioned between one of the one or more articulating clamps and one of the first and second rings, the dynamization washer arranged and configured to enable micro-motion of the clamp to the ring.

20. The kit according to claim 19, wherein the one or more dynamization washers include an opening passing therethrough arranged and configured to enable the stem of the articulating clamp to pass therethrough, the dynamization washer including a containment cup and a damper, the containment cup including an outer ledge defining a pocket for receiving at least a portion of the damper therein, the damper being arranged and configured to compress to enable micro-motion of the articulating clamp relative to the ring.

21. A kit for use with an external fixation system to one of facilitate conversion of the external fixation system into a static frame, enable temporary removal of one or more struts from the external fixation system to provide a larger visualization or working window, or enable construction of a static frame, the kit comprising:
    first and second rings arranged and configured to be coupled to a patient's bone, the first and second rings being arranged and configured to be coupled to each other via a plurality of external adjustable length struts, each of the first and second rings including a plurality of openings formed therein;
    one or more rods arranged and configured to span between the first and second rings;

one or more articulating clamps arranged and configured to couple one of the one or more rods to one of the first and second rings; and one or more dynamization washers arranged and configured to be positioned between one of the one or more articulating clamps and one of the first and second rings, the dynamization washer arranged and configured to enable micro-motion of the clamp to the ring;

wherein each of the one or more articulating clamps include a stem arranged and configured to be received within one of the openings formed in one of the first and second rings.

22. The kit according to claim 21, wherein:

at least one of the one or more articulating clamps includes a clamp portion arranged and configured to engage the rod spanning the first and second rings via a snap-fit or friction fit connection;

at least one of the one or more articulating clamps includes a body portion and a clamp portion, the body portion including the stem arranged and configured to be received within the opening formed in one of the first and second rings; and the clamp portion is arranged and configured to move relative to the body portion to enable a position of the connected ring to be adjusted relative to the rod spanning the first and second rings.

23. The kit according to claim 22, wherein the stem includes an externally threaded post arranged and configured to receive a threaded nut.

24. The kit according to claim 22, wherein the clamp portion includes first and second jaw members in facing arrangement, the first and second jaw members arranged and configured to receive the rod spanning the first and second rings.

25. The kit according to claim 24, wherein the clamp further includes a bolt including an externally threaded rod and an enlarged spherical head portion, the body portion includes a bore arranged and configured to at least partially receive the enlarged spherical head portion, the bolt is arranged and configured to couple the clamp portion to the body portion while enabling the clamp portion to articulate relative to the body portion.

26. The kit according to claim 25, wherein the clamp further comprises a threaded nut, the externally threaded rod of the bolt passing through the first and second jaw members so that engagement of the threaded nut with the externally threaded rod of the bolt secures a position of the rod spanning between the first and second rings between the first and second jaw members.

27. The kit according to claim 25, wherein the clamp further comprises a set screw arranged and configured to interact with the enlarged spherical head portion so that tightening of the set screw fixes a position of the clamp portion relative to the body portion.

28. The kit according to claim 21, wherein the one or more dynamization washers include an opening passing therethrough arranged and configured to enable the stem of the articulating clamp to pass therethrough, the dynamization washer including a containment cup and a damper, the containment cup including an outer ledge defining a pocket for receiving at least a portion of the damper therein, the damper being arranged and configured to compress to enable micro-motion of the articulating clamp relative to the ring.

* * * * *